(12) United States Patent
Lee et al.

(10) Patent No.: US 6,777,564 B2
(45) Date of Patent: Aug. 17, 2004

(54) ANTHRAQUINONE COMPOUND

(75) Inventors: Lain-Tze Lee, Hsingchu (JP); Jinun-Ban Yeh, HsingChu (JP)

(73) Assignee: Industrial Technology Research Institute, Hsinchu (TW)

( * ) Notice: Subject to any disclaimer, the term of this patent is extended or adjusted under 35 U.S.C. 154(b) by 100 days.

(21) Appl. No.: 10/022,411

(22) Filed: Dec. 20, 2001

(65) Prior Publication Data

US 2003/0149092 A1 Aug. 7, 2003

(51) Int. Cl.⁷ .............................................. C07D 307/34
(52) U.S. Cl. ..................................... 552/261; 514/683
(58) Field of Search ........................... 552/261; 514/683

(56) References Cited

FOREIGN PATENT DOCUMENTS

WO          WO91/00265      *  1/1991

* cited by examiner

*Primary Examiner*—Paul J. Killos
(74) *Attorney, Agent, or Firm*—Bacon & Thomas

(57) ABSTRACT

A novel compound with anthraquinone structure and having the following foluma (I):

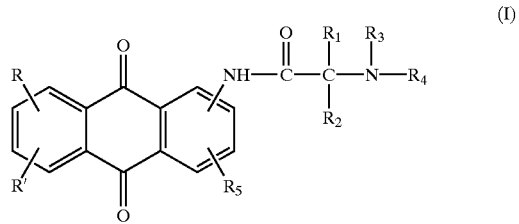

wherein $R_1$, $R_2$ and $R_3$ each independently is hydrogen, hydroxy, amino or $C_{1-6}$ alkyl group; $R_4$ is hydrogen, $C_{1-18}$ alkyl carbonyl, $C_{1-6}$ alkyl group substituted by at least a functional group; $R_5$ is hydrogen amino or a group of the following formula

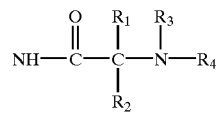

wherein $R_1$, $R_2$, $R_3$ and $R_4$ are defined as the above; and R and R' each independently is hydrogen, hydroxyl, amino, $C_{1-6}$ alkyl group or a group of the following formula

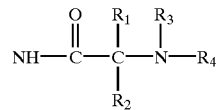

wherein $R_1$, $R_2$, $R_3$ and $R_4$ are defined as the above.

24 Claims, No Drawings

ANTHRAQUINONE COMPOUND

BACKGROUND OF THE INVENTION

1. Field of the Invention

The present invention relates to a novel anthraquinone compound, and more particularly to a novel anti-tumour anthraquinone compound.

2. Description of the Prior Art

The netropsin and its derivatives having polypyrrol molecular skeleton are known as effective or potential anti-virus compounds. Netropsin and its derivatives are proved to be effective to increase the survival rate of the animals infected by virus (e.g. mice infected by influenza A or B, mice infected by neutropic vaccinia virus or pigs infected by flu virus). The anti-virus ability of netropsin and its derivatives perhaps arises from the interaction between the DNA of virus and the guanido acetamide group of netropsin and its derivatives. It is thought that the guanido acetamide group of netropsin and its derivatives weaken the interaction between DNA polymerase and the DNA molecules. However, although the anti-virus ability of netropsin and its derivatives is proved, netropsin and its derivatives are not potential compounds for curing cancer, due to the reasons that the effect of the medication is unclear, the synthesis of the compound is difficult, the solubility of the compound is poor, and no anti-cancer ability of the compound is reported.

On the other hand, anthraquinone and its derivatives are used for anti-cancer purposes. Since the molecules of anthraquinone and its derivatives can insert into the double helix structure of DNA to interfere the replication of DNA, so that the proliferation of cancer cell can be further inhibited. However, most anthraquinone and its derivatives are highly toxic and with poor chemical selectivity.

Therefore, it may be an improvement to design and prepare a molecule to own the above effects simultaneously by combining anthraquinone and guanidoacetamide or benzyl carbamidoacetamide to selectively inhibit the replication of certain DNA, so that the proliferation of cancer cells can be selectively inhibited.

Accordingly, the present invention discloses novel anthraquinone compounds which have excellent selectivity, anti-virus and anti-cancer activity.

SUMMARY OF THE INVENTION

An object of the present invention is to provide a novel compound having an anthraquinone and a guanidoacetamide or benzyl carbarmidoacetamide group.

Another object of the present invention is to provide an anti-cancer pharmaceutic composition contains a novel anti-cancer compound having an anthraquinone and a guanidoacetamide or benzyl idoacetamide group.

One aspect of the present invention relates to a novel compound of the following formula (I),

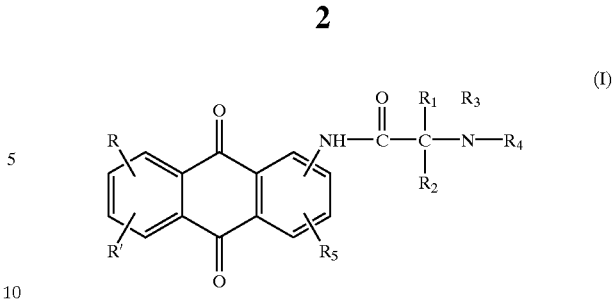

wherein $R_1$, $R_2$ and $R_3$ each independently is hydrogen, hydroxy, amino or $C_{1-6}$ alkyl group; $R_4$ is hydrogen, $C_{1-18}$ alkyl carbonyl, $C_{1-6}$ alkyl group substituted by at least a functional group, said functional group is selected from the group consisting of hydroxyl, amino, carbado, carbazoyl, fonnyl, carbamyl, carboxyl, carbonyl, or a group of the $$\begin{array}{c} NH \\ \| \\ -C-NH_2 \cdot HX \end{array}$$

wherein X is fluoro, chloro, bromo, iodo, or a group of the following formula $$\begin{array}{c} O \\ \| \\ -C-O-(CH_2)_{\overline{n}}-R_6 \end{array}$$

wherein n is 1, 2, or 3, $R_6$ is hydrogen or aromatic alkyl, or a group of the following formula $$\begin{array}{cc} O & O \\ \| & \| \\ -C-(CH_2)_l-(NH)_{\overline{m}}-C-O-(CH_2)_{\overline{n}}-R_6 \end{array}$$

wherein l is 1, 2, or 3, m is 0 or 1, n and $R_6$ are defined as the above; $R_5$ is hydrogen, amino or a group of the following formula $$\begin{array}{ccc} O & R_1 & R_3 \\ \| & | & | \\ NH-C-C-N-R_4 \\ & | \\ & R_2 \end{array}$$

wherein $R_1$, $R_2$, $R_3$ and $R_4$ are defined as the above; and R and R' each independently is hydrogen, hydroxyl, amino, $C_{1-6}$ alkyl group or a group of the following formula $$\begin{array}{ccc} O & R_1 & R_3 \\ \| & | & | \\ NH-C-C-N-R_4 \\ & | \\ & R_2 \end{array}$$

wherein $R_1$, $R_2$, $R_3$ and $R_4$ are defined as the above.

In the novel compound of the present invention, $R_1$, $R_2$ and $R_3$ are preferably hydrogen or amino; $R_4$ is preferably hydrogen or a group of the following formula; and $$\begin{array}{c} NH \\ \| \\ -C-NH_2 \end{array}$$

R and R' each independently is hydrogen, amino or a group of the following formula

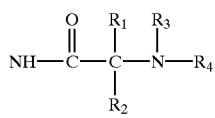

wherein $R_1$, $R_2$, $R_3$ and $R_4$ are defined as the above.

In a preferred embodiment of the novel compound of the present invention, the $R_4$ is a group of the following formula

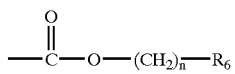

wherein n is 1, 2 or 3; $R_6$ is hydrogen, 1-naphthyl, 2-naphthyl or a group of the following formula

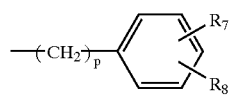

wherein p is 0, 1, 2, or 3; $R_7$ and $R_8$ each independently is hydrogen, hydroxyl, carbado, carbamyl, carboxyl, carbonyl, formyl, mercapto, methylthio, thioureido, thiocyanato, sulfoamoyl, sulfo, phosphono, fluoro, chloro, bromo, iodo, cyano, trifluoro methyl, $C_{1-6}$ alkyl group, $C_{1-6}$ alkoxy group, dimethyl amino, and benzyloxy, $C_{1-18}$ alkoxycarbonyl, or arylmethoxycarbonyl, wherein said aryl group is phenyl, 2-methoxyphenyl, 4-methoxyphenyl, 2-fluorophenyl, 4-fluorophenyl, 2-chlorophenyl, 4-chlorophenyl, 2-bromophenyl, 4-bromophenyl, 1-naphthyl, 2-naphthyl, 9-fluorenyl, or pentafluorophenyl; and a pharmaceutically acceptable salt thereof.

It is further preferred that $R_4$ is a group of the following formula

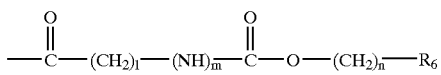

wherein l is 1; m is 0; n is 1; $R_6$ is a group of the following formula

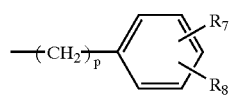

wherein p is 0 or 1; $R_7$ and $R_8$ each independently is hydrogen, hydroxyl, carbamyl, carboxyl, carbonyl, formyl, mercapto, methylthio, thioureido, thiocyanato, sulfoamoyl, sulfo, phosphono, fluoro, chloro, bromo, iodo, cyano, trifluoro methyl, $C_{1-6}$ alkyl group, $C_{1-6}$ alkyl oxide group, dimethyl amine, and benzyloxy, $C_{1-18}$ alkoxycarbonyl, or aryl-methoxycarbonyl, wherein said aryl group is phenyl, 2-methoxyphenyl, 4-methoxyphenyl, 2-fluorophenyl, 4-fluorophenyl, 2-chlorophenyl, 4-chlorophenyl, 2-bromophenyl, 4-bromophenyl, 1-naphthyl, 2-naphthyl, 9-fluorenyl, or pentafluorophenyl; and a pharmaceutically acceptable salt thereof.

The present invention further provides a pharmaceutic composition which contains (1) an effective amount of formula (I) compound described above, and (2) one or more pharmaceutically acceptable carriers. An effective amount depends upon the condition being treated, the route of administration chosen, and the specific activity of the compound used, and ultimately will be decided by the attending physician or veterinarian.

The pharmaceutic composition of the present invention is an pharmaceutic composition with anti-virus ability. It can also effectively inhibit the proliferation of cancer cells. Preferably, the pharmaceutic composition of the present invention can be used for curing lung cancer, leukemia or brain cancer or AIDS.

DETAILED DESCRIPTION OF THE PREFERRED EMBODIMENTS

The compounds of formula (I) of the present invention can be prepared by the following steps (as shown in scheme A or B),

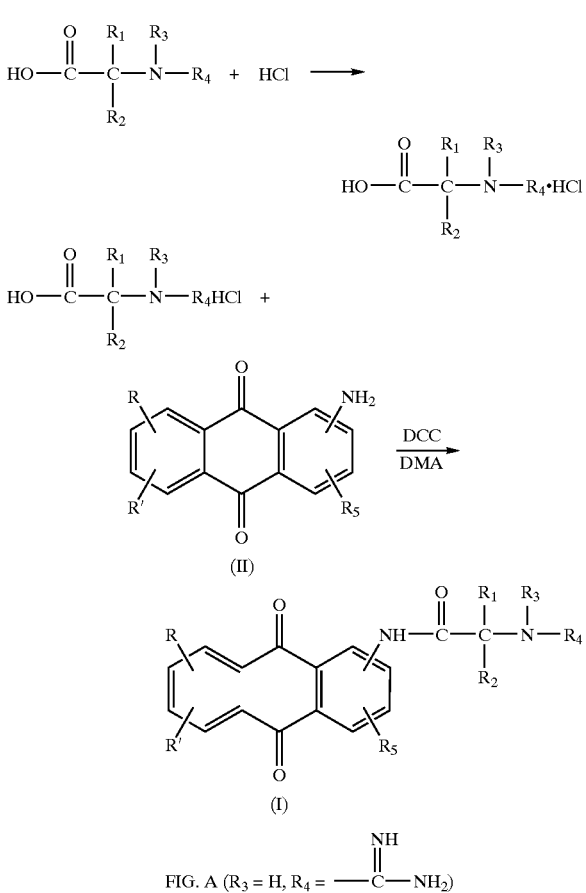

FIG. A ($R_3$ = H, $R_4$ = )

wherein R, R', $R_1$, $R_2$, $R_3$, $R_4$ and $R_5$ are defined as the above.

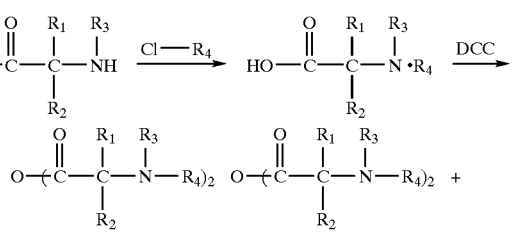

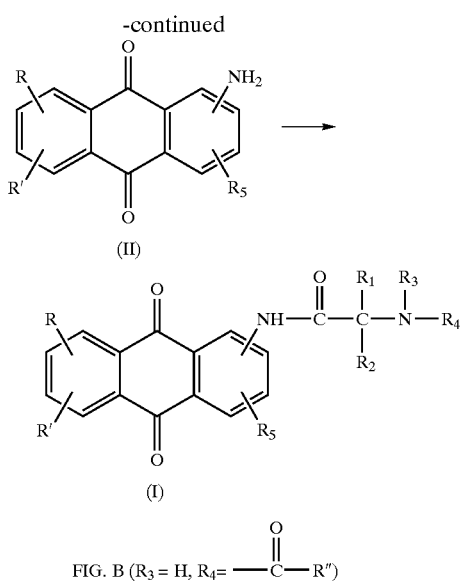

FIG. B ($R_3$ = H, $R_4$ = —C(=O)—R")

wherein R, R'$R_1$, $R_2$, $R_3$, $R_4$ and $R_5$ are defined as the above.

More detailed examples are used to illustrate the present invention, and these examples are used to explain the present invention. The examples below, which are given simply by way of illustration, must not be taken to limit the scope of the invention.

EXAMPLE 1

Preparation of 1-benzyl carbamidoacetamidoanthraquinone

DCC (N, N'-dicyclohexyl carbodimide) (0.2 g, 0.001 mole) and dichloromethane (5 ml) were added into a reaction bottle, and the temperature thereof was cooled to 0–5° C. by ice bath. Benzyl carbamidoacetate (0.42 g, 0.002 mole) was then added and stirred at low temperature for 30 minutes to form acid anhydride and white precipitate of DCU. Then 1-amino anthraquinone (0.22 g, 0.001 mole) was added at room temperature and stirred overnight. From HPLC analysis, it was known that the reaction was complete. The insoluble DCU was removed by filtering and the residue was washed by dichloromethane and acetone. A dark solid was obtained after the filtrate was concentrated through a rotary evaporator. After purified through silica gel chromatography with eluent consisted of n-hexane and ethyl acetate, 0.37 g of yellow needlelike crystal (75%) was obtained, 200M $^1$H NMR (CDCl$_3$) δ64.2 (d,2H), 5.2(s,2H), 5.6(b, 1H), 7.2–8.3(m,12H), 9.1(d,1H).

EXAMPLE 2

Preparation of 4-amino-1-guanido acetamidoanthraquinone

DCC (1.03 g, 0.005 mole) was added into a reaction bottle and the bottle was sealed immediately. DCC was dissolved therein. Guanidoacetic acid hydrochloride (0.765 g, 0.005 mole) was then added and stirred to get a precipitate. 1,4-Diarino anthraquinone (0.49 g, 0.0025 mole) was then added and stirred at room temperature for 10 hours. From the HPLC analysis, it was known that the product yield was about 91%. Proper amount of DCC was supplemented and stirred until the yield was constant. DMA (100 ml) was added into the concentrate for dissolving product, wherein insoluble DCU was removed by filtering. The filtrate was concentrated under reduced pressure at 95° C. to remove DMA. Water (400 ml) was added into the concentrate for dissolving product, wherein insoluble DCU was removed by filtering. Acetone (100 ml) was then added to dissolve the residual 1-amino anthraquinone followed by filtrating. After recrystalizing in methanol and drying under vacuumn at 80° C., 0.36 g of red-brown 4-amino-1-guanido acetamidoanthraquinone crystal was obtained, 200M $^1$H NMR δ 6 4.2(s,2H), 7.2–8.4(m,10H), 8.7(d,1H), 12.6(s, 1H).

EXAMPLE 3

Preparation of 5-amino-1-guanido acetamidoanthraquinone

DCC (1.03 g, 0.005 mole) and DMA (10 ml) were added into a reaction bottle and stirred until fully dissolving. Guanidoacetic acid hydrochloride (0.765 g, 0.005 mole) was added and stirred to get a precipitate. 1.5-Diamino anthraquinone (0.49 g, 0.0025 mole) was then added and stirred at room temperature for 10 hours. Proper amount of DCC was supplemented and stirred until the yield was constant. From the HPLC analysis, it was known that the product yield was about 69%. The solution was concentrated under reduced pressure at 95° C. to remove DMA. Water (400 ml) was added to dissolve the product, and the insoluble DCU was removed by filtering. Acetone (100 ml) was then added to dissolve the residual anthraquinone followed by filtrating. After recrystalizing in methanol and drying under vacuumn at 80° C., 0.28 g of red-brown 5-amino-1-guanido acetamidoanthraquinone crystal was obtained, 200M $^1$H NMR δ 4.3(s,2H), 7.2–8.4(m, 10H), 8.9 (d,1H), 12.4(s,1H).

EXAMPLE 4

Preparation of 2-guanidinoacetamido anthraquinone

DCC (1.03 g, 0.005 mole) and DMA (10 ml) were added into a reaction bottle and stirred until fully dissolving. Guanidoacetic acid hydrochloride (0.765 g 0.005 mole) was added and stirred to get a precipitate. 2-amino anthraquinone (0.45 g, 0.0025 mole) was then added and stirred at room temperature for 10 hours. From the HPLC analysis, it was known that the product yield was about 94.5%. DMA (100 ml) was added to dissolve the product, and the insoluble DCU was removed by filtering. Acetone (100 ml) was then added to dissolve the residual anthraquinone. After recrystalizing in methanol and drying under vacuumn at 80° C., 0.4 g of red-brown 2-guanido acetamidoanthraquinone crystal was obtained, 200M $^1$H NMR δ(d$_6$-DMSO), 4.2(s,2H), 5.6(d,1H), 7.2–8.3(m, 11H), 8.5(s,1H).

EXAMPLE 5

Preparation of 4-amino-1-benzyl Carbamidoacetamidoanthraquinone

DCC (0.2 g, 0.001 mole) and dichloromethane (5 ml) were added into a reaction bottle, and the temperature thereof was cooled to 0–5° C. by ice bath. Benzyl carbamidoacetate (0.42 g, 0.002 mole) was then added and stirred at low temperature.for 30 minutes to form acid anhydride and white precipitate of DCU. Then 1,4-Diamino anthraquinone (0.23 g, 0.001 mole) was added at room temperature and stirred overnight. From HPLC analysis, it was known that the reaction was complete. The insoluble DCU was removed by filtering. The filtrate was washed by dichloromethane and acetone. A dark solid was obtained as after filtrate was concentrated through a rotary evaporator. After purified through silica gel chromatography with eluent consisted of n-hexane and ethyl acetate, 0.37 g of yellow needlelike crystal (86%) was obtained, 200M $^1$H NMR δ (CDCl$_3$) 4.1(d,2H), 5.3(s,2H), 7.3–8.5 (m,13H), 9.1(d,1H), 13.1(s, 1H).

EXAMPLE 6

Preparation of 1-amino-2-guanido acetamidoanthraquinone

DCC (1.03 g, 0.005 mole) was added into a reaction bottle and The bottle was sealed immediately. DMA (10 ml) was dissolved therein. Guanidoacetic acid hydrochloride (0.765 g, 0.005 mole) was then added and stirred to get a precipitate. 1,2-Diamino anthraquinone (0.49 g, 0.0025 mole) was then added and stirred at room temperature for 10 hours. From the HPLC analysis, it was known that the product yield was about 85%. Proper amount of DCC was supplemented and stirred until the yield was constant. The solution was concentrated under reduced pressure at 95° C. to remove DMA. Water (300 ml) was added into the concentrate for dissolving product, wherein insoluble DCU was removed by filtering. The water was then removed under reduced pressure. By recrystalizing in methanol and drying under vacuumn at 80° C., 0.06 g of red-brown 1-amino-2-guanido acetamidoanthraquinone crystal was obtained, 200M $^1$H NMR δ (d$_6$-DMSO), 4.2(s,2H), 7.2–8.3(m,9H), 10(b,1H).

EXAMPLE 7

Preparation of 6-amino-2-guanidoacetamidoanthraquinone

DCC (1.03 g, 0.005 mole) and DMA(10 ml) were added into a reaction bottle and stirred until fully dissolving. Guanidoacetic acid hydrochloride (0.765 g, 0.005 mole) was added and stirred to get a precipitate. 2,6-Diamino anthraquinone (0.49 g, 0.0025 mole) was then added and stirred at room temperature for 10 hours. From the HPLC analysis. it was known that the product yield was about 87%. Proper amount of DCC was added and stirred until the yield is constant. DMA was removed under reduced pressure at 95° C. Water (400 ml) was added to dissolve the product, and the insoluble DCU was removed by filtering. After removing water by evaporizing, recrystalizing in methanol, and drying under vacuumn at 80° C., 0.1 g of dark red 6-amino-2-guanido acetamidoanthraquinone crystal was obtained.

EXAMPLE 8

Preparation of 2,6-di(guanidino acetamido) anthraquinone

DCC (2.06 g, 0.01 mole) and DMA(10 ml) were added into a reaction bottle and stirred until fully dissolving. Guanido acetic acid hydrochloride (1.53 g, 0.01 mole) was added and stirred to get a precipitate. 2,6-diamino anthraquinone (0.49 g, 0.0025 mole) was then added and stirred at room temperature for 10 hours. Proper amount of DCC was supplemented and stirred until the product yield was constant known from the HPLC analysis. Then DMA was removed under reduced pressure at 95° C. Water (400 ml) was added to dissolve the product, and insoluble DCU was removed by filtering. After recrystalizing in methanol and drying under vacuum at 80° C., 0.1 g of dark red 2,6-di(guanidino acetamido)anthraquinone crystal was obtained.

EXAMPLE 9

Preparation of 2-Benzyl Carbamidoacetamidoanthraquinone

DCC (0.2 g, 0.001 mole) and dichloromethane (5 ml) were added into a reaction bottle, and the temperature thereof was reduced to 0–5° C. by ice bath. benzyl carbamidoacetate (0.42 g, 0.002 mole) was then added and stirred at low temperature for 30 minutes to form acid anhydride and white DCU precipitate. 2-Amino anthraquinone (0.22 g, 0.001 mole) was added at room temperature and stirred overnight. From the HPLC analysis, it was known that the reaction was complete. The insoluble DCU was removed by filtrating, and the residue was washed by dichloromethane and acetone. The filtrate was concentrated by rotary evaporator to get dark solid. After purified by silica gel chromatography with eluent consisted of n-hexane and ethyl acetate, 0.27 g of yellow-brown needlelike crystal was obtained (65%), 200M $^1$H NMR δ (CDCl$_3$) 4.1(d,2H), 5.2(s,2H), 6.5(b, 1H), 7.2–8.3(m,12H), 10.2(s,1H).

EXAMPLE 10

Preparation of 1,2-di(guanidino acetamido) anthraquinone

DCC (2.06 g, 0.01 mole) and DMA(10 ml) were added into a reaction bottle and stirred until fully dissolving. Guanidoacetic acid hydrochloride (1.53 g, 0.01 mole) was added and stirred to get a precipitate. 1,2-Diamino anthraquinone (0.49 g, 0.0025 mole) was then added and stirred at room temperature for 10 hours. Proper amount of DCC was supplemented and stirred until the yield was constant known from HPLC analysis. DMA was then removed under reduced pressure at 95° C. Water (400 ml) was added to dissolve product, and insoluble DCU was removed by filtering. After recrystalizing in methanol and dried under vacuum at 80° C., 0.06 g of red-brown 1,2-di (guanidino acetamido)anthraquinone crystal was obtained.

Test:

The compounds were further screened on 60 human cancer cell lines by Developmental Therapeutics Program Human Tumor Cell Line Screen set up by the National Cancer Institute of the U. S. A. The screening procedures are described briefly hereinafter. Cell suspensions that were diluted according to the particular cell type and the expected target cell density (5000–40,000 cells per well based on cell growth characteristics) were added by pipet (100 μL) into 96-well microtiterplates. Inoculates were allowed a preincubation period of 24 hours at 37° C. for stabilization. Dilutions at twice the intended test concentration were added in 100 μL aliquots to the microtiter plate wells at time zero. Usually, test compounds were evaluated at five 10-fold dilutions. In routine testing, the highest well concentration was $10^{-4}$ M, but for the standard agents the highest well concentration used depended on the agent. Incubations lasted for 48 hours in 5% $CO_2$ atmosphere and 100% humidity. The cells were assayed by using the sulforhodamine B assay. A plate reader was used to read the optical densities, and a microcomputer processed the optical densities into the special concentration parameters. The results of these tests with representative compounds of the present invention appear in Table 1 and 2

TABLE 1

The anti-cancer activity test results for Examples 1–10

IC$_{50}$ (μg/ml)

| Example | BC 1 | HT | Lu1 | Mel2 | Col2 | KB | KB-V (+VLB) | KB-V (-VLB) | P-388 | A431 | LNCaP | ZR-75-1 | U373 |
|---|---|---|---|---|---|---|---|---|---|---|---|---|---|
| 1 | >20 | 13.9 | >20 | >20 | >20 | >20 | 3.8 | >20 | >5 | >20 | 14.7 | >20 | >20 |
| 2 | 1.6 | 2.0 | 3.1 | 4.4 | 4.2 | 1.2 | 16.0 | >20 | >5 | 0.4 | 4.1 | 3.4 | 0.6 |
| 3 | 3.0 | 2.5 | 9.3 | 12.0 | 4.7 | 4.2 | 13.2 | >20 | >5 | 0.2 | 9.0 | 1.7 | 1.0 |
| 4 | 4.9 | 2.1 | 14.1 | 9.8 | 12.1 | 2.9 | 7.5 | >20 | >5 | 0.8 | 12.5 | 3.6 | 0.88 |
| 5 | >20 | >20 | >20 | >20 | >20 | >20 | 2.9 | >20 | >5 | >20 | >20 | >20 | >20 |
| 6 | 7.8 | 4.5 | >20 | >20 | >20 | 5.9 | 7.9 | >20 | >5 | 0.9 | >20 | 6.9 | 2.0 |
| 7 | 3.6 | 1.6 | >20 | 6.8 | 3.2 | 1.2 | >20 | >20 | 1.1 | 0.6 | 6.3 | 3.3 | 0.4 |
| 8 | 5.0 | 6.0 | 12.2 | 12.7 | 3.3 | 1.4 | >20 | >20 | >5 | 5.8 | 7.2 | 7.0 | 8.6 |
| 9 | 6.4 | 8.3 | 9.6 | 15.1 | 9.6 | 19.2 | 1.4 | >20 | >5 | 1.7 | >20 | 6.4 | 4.7 |
| 10 | 10.2 | 8.9 | >20 | >20 | >20 | 3.2 | 6.3 | >20 | >5 | 1.7 | 18.0 | >20 | 6.9 |

BC-1: human breast cell
HT-1088: human fibrosarcoma cell
Lu1: human lung cell
Mel: human melanoma cell
Col2: human colon cell
KB: human oral epidormaid Carcinama cell
KB-V: drug resisteant KB cell
VLB: vinblastine
P-388: mouse lymphaid Macrophage cell
A431: human squamous cell
LNCaP: human prostate cell
ZR-75-1: human breast cell
U373: human glioma cell

TABLE 2

The anti-virus activity test results for compounds of Examples 1–10 at 200 μg/ml to HIV-1 RT(p66)

| Example | activity inhibition (%) | IC$_{50}$ (μg/ml) |
|---|---|---|
| 1 | 47.0 | — |
| 2 | 99.5 | 8.72 |
| 3 | 99.6 | 6.93 |
| 4 | 99.4 | 18.9 |
| 5 | 23.0 | — |
| 6 | 99.7 | 40.1 |
| 7 | 99.7 | 12.5 |
| 8 | 29.3 | — |
| 9 | 53.4 | — |
| 10 | 92.3 | 30.3 |

According to Table 1, the compounds of formula (I) in the present invention are medically effective to many human cancer cell lines and show significant cytotoxic activity at lower concentrations. Particularly, the compounds of Examples 2, 3, 4, 6, 7, 8 and 10 with a guanido group were more effective to most cancer cell lines. Therefore, the compounds of formula (I) in the present invention indeed had cytotoxic activity to human cancer cell lines.

Furthermore, according to Table 2, the compounds of formula (I) with guanido groups such as compounds of Example 2, 3, 4, 6, 7 and 10 show excellent effect on activity inhibition at the concentration of 200 μg/ml, and IC$_{50}$ thereof were quite low. As for the compounds of Example 1, 5 and 9 with benzylureido group, they also show anti-virus ability but not so strong as the others.

The novel formula (I) compound of the present invention is effective for inhibiting human cancer cells. The pharmaceutical compositions contain the formula (I) compound and a pharmaceutically acceptable carrier is potentially effective for curing lung cancer, leukemia or brain cancer or AIDS.

From the foregoing description, one skilled in the art can easily ascertain the essential characteristics of this invention, and without departing from the scope thereof, can make various changes and modifications of the invention to adapt it to various usages and conditions. Thus, other embodiments are also within the claims.

What is claimed is:

1. A compound of the following formula (I):

$$R\text{-}\underset{O}{\underset{\|}{C}}\text{-anthraquinone-}NH-\underset{O}{\underset{\|}{C}}-\underset{R_2}{\underset{|}{C}}(R_1)-N(R_3)-R_4 \quad (I)$$

wherein:

R$_1$, R$_2$ and R$_3$ each independently is hydrogen, hydroxyl, amino or C$_{1-6}$ alkyl group;

R$_4$ is hydrogen, C$_{1-18}$ alkyl carbonyl, C$_{1-6}$ alkyl group substituted by at least a functional group, said functional group is selected from the group consisting of hydroxyl, amino, carbado, carbazoyl, formyl, carbamyl, carboxyl, carbonyl, or a group of the following formula $$-\underset{\|}{\underset{NH}{C}}-NH_2 \cdot HX$$

wherein X is fluoro, chloro, bromo, lodo, a group of the following formula

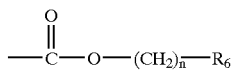

wherein n is 1, 2, or 3, $R_6$ is hydrogen or arylalkyl, or a group of the following formula

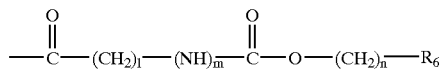

wherein l is 1, 2, or 3, m is 0 or 1, n and $R_6$ is defined as the above; $R_5$ is hydrogen amino or a group of the following formula

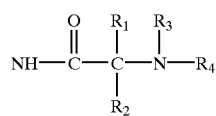

wherein $R_1$, $R_2$, $R_3$ and $R_4$ are defined as the above; and R and R' each independently is hydrogen, hydroxyl, amino, $C_{1-6}$ alkyl group or a group of the following formula

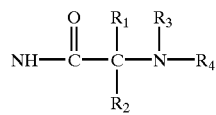

wherein $R_1$, $R_2$, $R_3$ and $R_4$ are defined as the above.

2. The compound of claim 1, wherein $R_1$, $R_2$, and $R_3$ each independently is hydrogen or amino group.

3. The compound of claim 1, wherein R and R' each independently is hydrogen, amino group or a group of the following formula

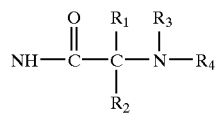

wherein $R_1$, $R_2$, and $R_3$ each independenly is hydrogen or amino group; and $R_4$ is hydrogen or a group of the following formula

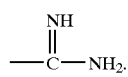

4. The compound of claim 1, wherein $R_1$ and $R_2$ is hydrogen.

5. The compound of claim 1, wherein $R_4$ is a group of the following formula

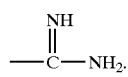

6. The compound of claim 1, wherein $R_4$ is a group of the following formula

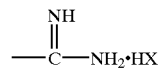

wherein X is fluoro, chloro, bromo or Iodo.

7. The compound of claim 1, wherein $R_4$ is a group of the following formula

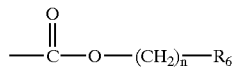

wherein n is 1, 2 or 3; $R_6$ is hydrogen, 1-naphthyl, 2-naphthyl or a group of the following formula

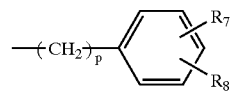

wherein p is 0, 1, 2, or 3; $R_7$ and $R_8$ each independently is hydrogen, hydroxyl, carbado, carbamyl, carboxyl, carbonyl, formyl, mercapto, methylthlo, thIoureido, thiocyanato, sulfoamoyl, sulfo, phosphono, fluoro, chloro, bromo, Iodo, cyano, trifluoro methyl, $C_{1-6}$ alkyl group, $C_{1-6}$ alkoxy group, dimethyl amino, and benzyloxy, $C_{1-18}$ alkoxycarbonyl, or arylmethoxycarbonyl, wherein said aryl group is phenyl, 2-methoxyphenyl, 4-methoxyphenyl, 2-fluorophenyl, 4-fluorophenyl, 2-chlorophenyl, 4-chlorophenyl, 2-bromophenyl, 4-bromophenyl, 1-naphthyl, 2-naphthyl, 9-fluorenyl, or pentafluorophenyl; and a pharmaceutically acceptable salt thereof.

8. The compound of claim 1, wherein $R_4$ is a group of the following formula

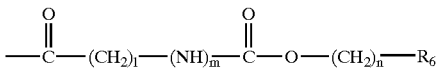

wherein l is 1, m is 0, n is 1; $R_6$ is a group of the following formula

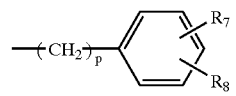

wherein p is 0 or 1; $R_7$ and $R_8$ each independently is hydrogen, hydroxyl, carbamyl, carboxyl, carbonyl, formyl, mercapto, $C_{1-6}$ alkyl group, $C_{1-6}$ alkoxy group, dimethyl amino, and benzyloxy, $C_{1-18}$ alkoxycarbonyl, or arylmethoxycarbonyl, wherein said aryl group is phenyl, 2-methoxyphenyl, 4-methoxyphenyl, 2-fluorophenyl, 4-fluorophenyl, 2-chlorophenyl, 4-chlorophenyl, 2-bromophenyl, 4-bromophenyl, 1-naphthyl, 2-naphthyl, 9-fluorenyl, or pentafluorophenyl; and a pharmaceutically acceptable salt thereof.

9. The compound of claim 1, wherein said formula (I) compound is 1-benzylcarbamidoacetamidoanthraquinone; and a pharmaceutically acceptable salt thereof.

10. The compound of claim 1, wherein said formula (I) compound is 4-amino-1-guanido acetamidoanthraquinone; and a pharmaceutically acceptable salt thereof.

11. The compound of claim 1, wherein said formula (I) compound is 5-amino-1-guanido acetamidoanthraquinone; and a pharmaceutically acceptable salt thereof.

12. The compound of claim 1, wherein said formula (I) compound is 2-guanidinoacetamido anthraquinone; and a pharmaceutically acceptable salt thereof.

13. The compound of claim 1, wherein said formula (I) compound is 4-amino-1-benzyl carbamidoacetamidoanthraquinone; and a pharmaceutically acceptable salt thereof.

14. The compound of claim 1, wherein said formula (I) compound is 1-amino-2-guanidoacetamidoanthraquinone; and a pharmaceutically acceptable salt thereof.

15. The compound of claim 1, wherein said formula (I) compound is 6-amino-2-guanido acetamidoanthraquinone; and a pharmaceutically acceptable salt thereof.

16. The compound of claim 1, wherein said formula (I) compound is 2,6-di(guanidino acetamido)anthraquinone; and a pharmaceutically acceptable salt thereof.

17. The compound of claim 1, wherein said formula (I) compound is 2-benzyl carbamidoacetamidoanthraquinone; and a pharmaceutically acceptable salt thereof.

18. The compound of claim 1, wherein said formula (I) compound is 1,2-di(guanidino acetamido)anthraquinone; and a pharmaceutically acceptable salt thereof.

19. An pharmaceutic composition for inhibiting the activities of cancer cells, which comprising an effective amount of formula (I) compound as described in claim 1, and a pharmaceutically acceptable carrier.

20. The pharmaceutic composition of claim 19, which is used for curing lung cancer, leukemia or brain cancer.

21. A pharmaceutic composition with anti-virus activity, which comprising an effective amount of formula (I) compound as described in claim 1, and one or more pharmaceutically acceptable carriers.

22. The pharmaceutical composition of claim 21, which is used inhibiting AIDS virus.

23. A method for preparing a compound of the following formula (I),

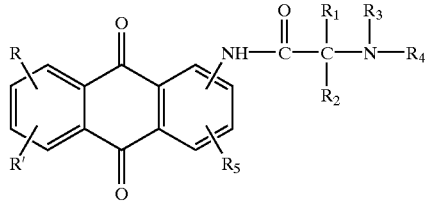

wherein:
$R_1$, $R_2$ and $R_3$ each independently is hydrogen, hydroxy, amino or $C_{1-6}$ alkyl group;

$R_4$ is hydrogen, $C_{1-18}$ alkyl carbonyl, $C_{1-6}$ alkyl group substituted by at least a functional group, said functional group is selected from the group consisting of hydroxy, amino, carbado, carbazoyl, formyl, carbamyl, carboxyl, carbonyl, or a group of the following formula

wherein X is fluoro, chloro, bromo, iodo, a group of the following formula

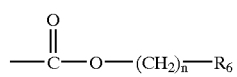

wherein n is 1, 2, or 3, $R_6$ is hydrogen or arylalkyl, or a group of the following formula

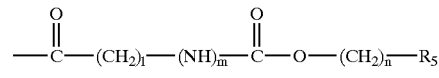

wherein l is 1, 2, or 3, m is 0 or 1, n and $R_6$ are defined as the above;

$R_6$ is hydrogen amino or a group of the following formula

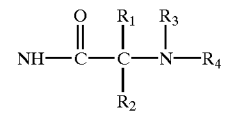

wherein $R_1$, $R_2$, $R_3$ and $R_4$ are defined as the above; and

R and R' each independently is hydrogen, hydroxyl, amino, $C_{1-6}$ alkyl group or a group of the following formula

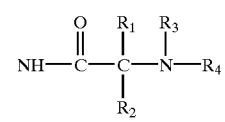

wherein $R_1$, $R_2$, $R_3$ and $R_4$ are defined as the above, which comprising:

a compound of the following formula (II)

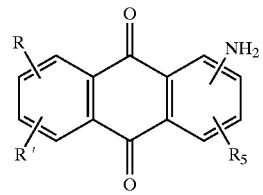

wherein n, R and R' are defined as the above with a compound of the following formula (III) or formula (IV)

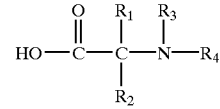

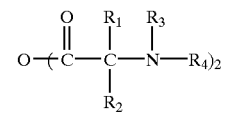

wherein $R_1$, $R_2$, $R_3$ and $R_4$ are defined as the above, in the presence of a coupling agent to proceed a condensation reaction.

24. The method of claim 23, wherein said coupling agent is N,N'-diisopropyl-carbodiimide, N,N'-dicyclohexyl carbodiimide, ethyl chloro-formate, carbony diimidazole or ECDI in a solvent.

* * * * *